United States Patent [19]

Takeno et al.

[11] Patent Number: 5,598,452
[45] Date of Patent: Jan. 28, 1997

[54] METHOD OF EVALUATING A SILICON SINGLE CRYSTAL

[75] Inventors: Hiroshi Takeno; Ryoji Hoshi; Satoshi Ushio; Takao Takenaka, all of Annaka, Japan

[73] Assignee: Shin-Etsu Handotai Co., Ltd., Tokyo, Japan

[21] Appl. No.: 524,453

[22] Filed: Sep. 6, 1995

[30] Foreign Application Priority Data

Sep. 8, 1994 [JP] Japan .................. 6-240630

[51] Int. Cl.$^6$ .................. G01N 23/207
[52] U.S. Cl. .................. 378/73; 378/71
[58] Field of Search .................. 378/70, 71, 73, 378/83, 87, 88

[56] References Cited

U.S. PATENT DOCUMENTS 5,073,918 12/1991 Kamon .................. 378/70
5,136,624 8/1992 Schneider et al. .

OTHER PUBLICATIONS

Kawado et al., "Influence of Crystal Imperfection on High–Resolution Diffraction Profiles of Silicon Single Crystals . . . ", *Appl. Phys. Lett.*, vol. 48, No. 20, pp. 2246–2248, May 20, 1991.

Hahn et al., "Effects of Heavy Boron Doping Upon Oxygen Precipitation in Czochralski Silicon", *J. Appl. Phys.*, vol. 64, No. 9, pp. 4454–4465, Nov. 1, 1988.

*Primary Examiner*—Don Wong
*Attorney, Agent, or Firm*—Evenson, McKeown, Edwards & Lenahan P.L.L.C.

[57] ABSTRACT

According to the invention, it is sought to provide a method of evaluating single crystal of silicon, which permits determination of the amount of precipitated oxygen of even a sample having been heat treated and with unknown initial interstitial oxygen concentration. X-rays radiated from X-ray source 7 is converted by slit 6 into a thin, parallel incident X-ray beam 3 to be incident on sample single crystal 1. After adjusting the angle θ1 of sample with respect to the incident X-ray beam such as to satisfy Bragg conditions, diffracted X-rays 4 produced by diffraction on the sample single crystal 1 are coupled from the back side thereof through X-ray receiving slit 8 to scintillator 5 for intensity measurement. The amount of precipitated oxygen is calculated from the measured diffracted X-ray intensity.

8 Claims, 2 Drawing Sheets

METHOD OF EVALUATING A SILICON SINGLE CRYSTAL

BACKGROUND OF THE INVENTION

1. Field of the Invention

This invention relates to a method of evaluating the amount of precipitated oxygen in a silicon wafer.

2. Description of the Prior Art

A semiconductor integrated circuit (IC) is manufactured by following process; on a mirror-polished silicon wafer (hereinafter referred to as silicon wafer), which is made of single crystal of silicon grown by the Czochralski method, the floating zone method, and etc. and has a thickness of about 0.5 mm, integrated circuit patterns such as diodes, transistors, MOS-FETs, resistors, capacitors and so on are formed, then the surface of the silicon wafer is covered with a thin insulating film followed by forming metal contacts and interconnections.

For the IC manufacture, polycrystalline silicon, for instance, is melted in a quartz crucible, and a single crystal rod which serves as seed crystal is brought from above the crucible into contact with the silicon melt while slowly rotating the rod. Silicon single crystal is thus grown by the Czochralski method. However, the single crystal thus grown inevitably contains about $10^{18}/cm^3$ of over-saturated interstitial oxygen. When the silicon wafer which contains interstitial oxygen is subsequently annealed at a low temperature of 800° C. or below and also at a high temperature of 1,000° C. or above, for instance, the interstitial oxygen is readily precipitated as oxides of silicon, thus generating numerous micro defects in the single crystal.

The micro defects suitably constitute getting cites of heavy metal impurities, etc., so long as they are found in the bulk of the wafer. However, when they exist in the vicinity of the wafer surfaces, they have direct adverse effects on the yield of device and so forth.

Therefore, the evaluation of the amount of precipitated oxygen in silicon single crystal is becoming increasingly important.

Heretofore, in case of silicon single crystal grown by the Czochralski method, the evaluation of the amount of precipitated oxygen after the single crystal has been heat treated, is made by using a Fourier transform type infrared absorption (FT-IR) method.

This method makes use of the absorption of light of a particular wavelength in the infrared wavelength range by interstitial oxygen atoms present in the silicon single crystal. In this method, the absorption spectrum in the infrared wavelength range is first determined, then the interstitial oxygen concentration is determined from the peak height of the spectrum, and then the amount $\Delta Oi$ of the precipitated oxygen is determined from the difference between the interstitial oxygen concentrations Oi(b) and Oi(a) in silicon wafer before and after a heat treatment thereon, respectively.

According to the prior art as described above, the amount of precipitated oxygen $\Delta Oi$ is determined from the difference between the interstitial oxygen concentrations Oi(b) and Oi(a) before and after the heat treatment. Therefore, with a sample which has been heat treated and in which the initial interstitial oxygen concentration is not known, it is impossible to determine the amount of precipitated oxygen.

In another aspect of the above prior art, as transmission process is adopted, in which infrared light transmitted through the silicon single crystal are detected. Therefore, although the amount of precipitated oxygen can be evaluated in the entire thickness of the sample, in a superficial region thereof to a certain depth non-destructive evaluation can not be made without making the sample thinner.

Further, in the case of low resistivity single crystal silicon which is doped with a high concentration of a dopant for resistivity control, infrared lights are absorbed pronouncedly by free carriers, so that they are difficult to be transmitted. Therefore, it is necessary to make the sample extremely thin, but this is unfeasible.

SUMMARY OF THE INVENTION

In the light of the above circumstances, it is an object of the invention to provide a method of evaluating single crystal silicon, which permits determination of the amount of precipitated oxygen even with a sample having been heat treated and having had an unknown initial interstitial oxygen concentration.

Another object of the invention is to provide a method of silicon single crystal evaluation, which permits non-destructive silicon evaluation of the amount of precipitated oxygen of in a superficial region of a sample to a certain depth thereof.

A further object of the invention is to provide a method of evaluating silicon single crystal, which permits non-destructive determination of the amount of precipitated oxygen in the same manner as above even with a low resistivity of silicon single crystal.

According to the invention, to attain the above objects there is provided a method of evaluating a silicon single crystal comprising the steps of; irradiating frontside surface of a preliminary heat treated sample silicon wafer with X-rays, taking out diffracted X-rays produced by Bragg diffraction at a particular lattice plane in said silicon wafer from backside surface, measuring the intensity of said diffracted X-ray, thereby preparing a correlation between the diffracted X-ray intensity and amount of precipitated oxygen of silicon wafers, characterized in: measuring the diffracted X-ray intensity of the heat treated sample silicon wafer and calculating the amount of precipitated oxygen thereof from the prepared correlation.

Suitably, the particular diffraction plane is designated by hkl, where h, k and l are indexes designated by an even number excluding zero, an even number including zero and zero, respectively.

Suitably, the index of the particular diffraction plane is 220, 440, 660, 880, 400, 800 or 1200.

Suitably, the prepared correlation is a relation between the ratio or difference between the diffracted X-ray intensity before the heat treatment and that after the heat treatment and the amount of precipitated oxygen under the assumption that the thickness of the silicon wafer is the same before and after the heat treatment.

Further, according to the invention there is provided a method of evaluating a silicon single crystal comprising the steps of; irradiating frontside surface of a preliminary heat treated sample silicon wafer with X-rays, taking out diffracted X-rays produced by Bragg diffraction at a particular lattice plane in said silicon wafer from the same surface as the incidence surface, measuring the intensity of said diffracted X-ray, thereby preparing a correlation between the diffracted X-ray intensity and amount of precipitated oxygen of silicon wafers, characterized in: measuring the diffracted X-ray intensity of the heat treated sample silicon wafer and calculating the amount of precipitated oxygen thereof from the prepared correlation.

Suitably, the particular lattice plane designated by hkl, where h, k and l are indexes designated by an even number excluding zero, an even number including zero and zero, respectively.

Suitably, the index of the particular lattice plane is 400, 800 or 1200.

Suitably, the prepared correlation is a relation between the ratio or difference between the diffracted X-ray intensities before and after the heat treatment and the amount of precipitated oxygen.

Functions according to the invention will now be described.

In the prior art example, the interstitial oxygen concentration of the same silicon wafer is measured before and after heat treatment, and the amount of precipitated oxygen was determined from the difference between the two measured values. A feature of the invention resides in that even with a silicon wafer which has been heat treated the amount of precipitation oxygen can be calculated by only measuring the diffracted X-ray intensity.

Thus, according to the invention the front surface of sillicon wafer is irradiated with X-rays, and diffracted X-rays which are produced by Bragg diffraction at a particular lattice plane are taken out from a surface different from the incidence surface for diffracted X-ray intensity measurement. Thus, the diffracted X-ray intensity is measured with respect to the entire thickness of sample.

Further, the amount of precipitated oxygen is calculated from the correlation between preliminarily obtained diffracted X-ray intensity and precipitated oxygen amount after heat treatment. Thus, the precipitated oxygen amount can be calculated simply by only measuring the diffracted X-ray intensity after the heat treatment.

Further, according to the invention the front surface of silicon wafer is irradiated with X-rays, and diffracted X-rays produced by Bragg diffraction at a particular lattice plane are taken out from the same surface as the incidence surface for diffracted X-ray intensity measurement. Thus, it is possible to obtain diffracted X-ray intensity measurement with respect to a superficial region of sample to a certain depth thereof from the incidence surface. This means that there is no need of making the sample thinner.

Further, the amount of precipitated oxygen is calculated from the correlation between the preliminarily obtained diffracted X-ray intensity and the amount of precipitated oxygen after the heat treatment. Thus, the amount of precipitated oxygen can be calculated simply by only measuring the diffracted X-ray intensity after the heat treatment.

Further, by preliminarily measuring and preserving the diffracted X-ray intensity Xb which has not been heat treated, using the diffracted X-ray intensity Xa after the heat treatment and Xb noted above, it is possible to calculate the diffracted X-ray intensity ratio (for instance Xa/Xb) or diffracted X-ray intensity difference (for instance Xa–Xb). Since the correlation between the diffracted X-ray intensity ratio or difference and the amount of precipitated oxygen is preserved, the amount of precipitated oxygen can be calculated from the preserved correlation.

It is a basis of the invention that the amount of precipitated oxygen and the diffracted X-ray intensity ratio or difference is in a good condition. In addition, it is to be particularly noted that it is confirmed by the inventor that the diffracted X-ray intensity of a silicon wafer which has not been heat treated is hardly influenced by the initial oxygen concentration, the resistivity, etc. and is substantially the same with silicon single crystal which are the same or substantially the same in the thickness, that is, the difference X-ray intensity of a silicon wafer which has not been heat treated approximately depends on the sole wafer thickness.

The diffracted X-ray intensity of the silicon wafer which has not been heat treated, has already been determined, and this value and the diffracted X-ray intensity of the silicon wafer after heat treatment are used to obtain the intensity ratio or difference so as to calculate the precipitated oxygen amount.

Thus, according to the invention the amount of precipitated oxygen can be determined non-destructively and quantitatively through measurement of the intensity of diffracted X-rays from a certain particular lattice plane of single crystal silicon by irradiating the crystal with X-rays. Particularly, with a sample after heat treatment the amount of precipitated oxygen can be calculated by merely measuring the diffracted X-ray intensity.

Further, it is possible to determine the amount of precipitated oxygen non-destructively not only over the integrity of the sample thickness but also in a sample region near the surface thereof.

Further, it is possible to easily make evaluation of the amount of precipitated oxygen in a low resistivity silicon single crystal of 0.1 Ωcm or below, which has been very difficult in the prior art.

DETAILED DESCRIPTION OF THE PREFERRED EMBODIMENTS

Figure 1:
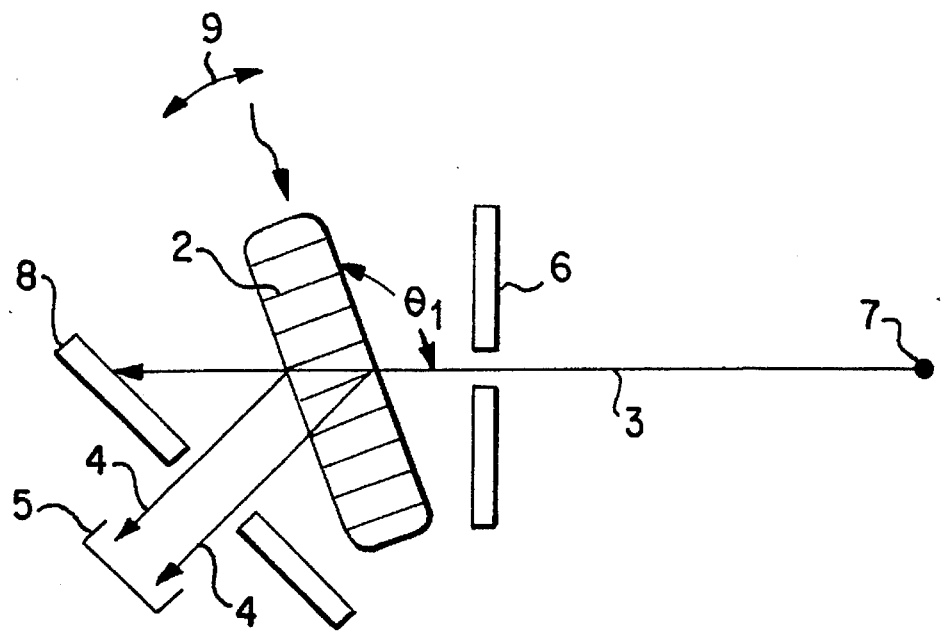
FIG. 1 is a schematic view illustrating a Laue case X-ray diffraction process used in the semiconductor crystal evaluation method according to the invention.

Now, the invention will be described in detail in connection with embodiments thereof illustrated in the drawings. Unless otherwise specified, the sizes, materials, shapes, relative positions, etc. of the constituent parts of the embodiments are shown without any sense of limiting the scope of the invention but as mere examples.

Figure 2:
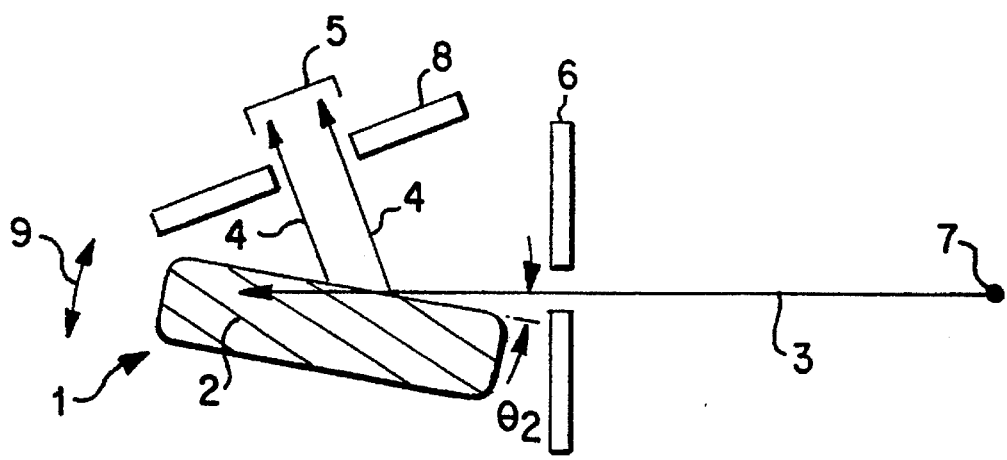
FIG. 2 is a schematic view illustrating a Bragg case X-ray diffraction process used in the semiconductor crystal evaluation method according to the invention.
Figure 3:
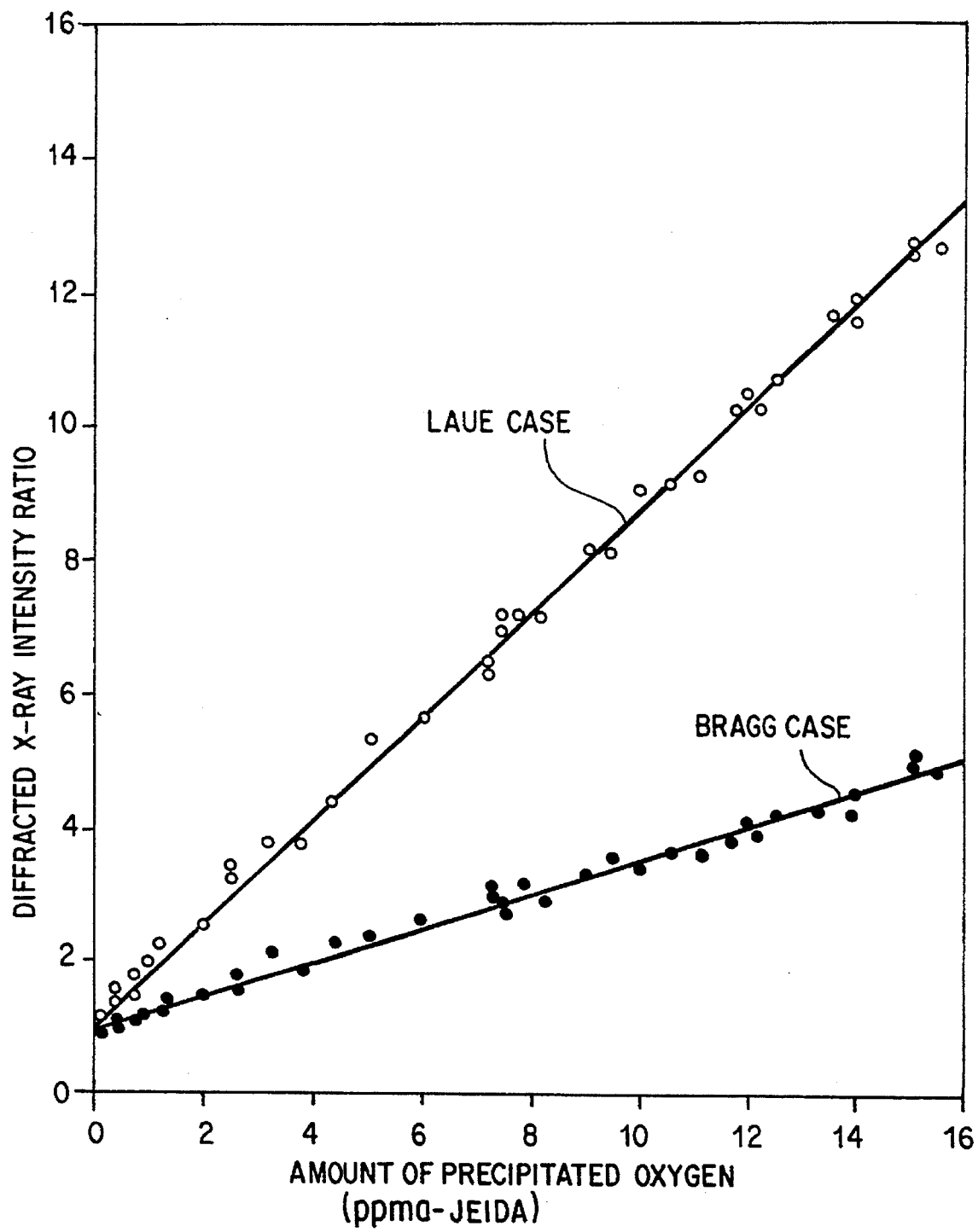
FIG. 3 is a graph showing the diffracted X-ray intensity ratio in Laue case 440 diffraction and the diffracted X-ray intensity ratio in Bragg case 400 diffraction, these intensity ratios being plotted against the amount of precipitated oxygen (based on the FT-IR process) of a heat treated silicon single crystal.

FIG. 1 is a view illustrating a Laue case X-ray diffraction process used for the method of evaluating semiconductor single crystal according to the invention. FIG. 2 is a view illustrating a Bragg case X-ray diffraction process used for the evaluation method. Table 1 summarizes the relation of diffracted X-ray intensity of both 440 diffraction in Laue case and 400 diffraction in Bragg case and the thickness of silicon wafers which have not been heat treated. FIG. 3 is a graph showing the 440 and 400 diffraction diffracted X-ray intensity ratios in the Laue and Bragg cases, respectively, of silicon single crystal having been heat treated with respect to the amount of precipitated oxygen amount based on the FT-IR method.

Referring to FIG. 1, X-ray radiated from an X-ray source 7 constituted by an X-ray generator is converted by an incident slit 6 into a thin, parallel incident X-ray beam 3 to be incident on a sample single crystal 1.

The sample single crystal 1 has diffraction lattice plane 2, and it can be rotated for adjusting its angle θ1 with respect to the incident X-ray beam 3.

An X-ray receiving slit 8 is provided for receiving diffracted X-ray having been diffracted by the sample single crystal 1 from the back side thereof. Behind the light receiving slit 8, scintillation counter 5 is provided for measuring the intensity of the diffracted X-rays 4.

FIG. 2 illustrates the X-ray diffraction process in the Bragg case. In the Figure, parts like those in FIG. 1 are designated by like reference numerals and symbols. X-rays radiated from X-ray source 7 are converted by incidence slit 6 into a thin, parallel incident X-ray beam 3 to be incident on sample single crystal 1.

The sample single crystal 1 has diffraction lattice plane 2, and it can be rotated for adjusting its angle θ2 with respect to the incident X-ray beam 3.

X-ray receiving slit 8 is provided on the front side of the sample single crystal 1 for receiving diffracted X-rays 4 from the single crystal 1 from the front side thereof. Behind the light receiving slit 8, a scintillation counter 5 is provided for measuring the intensity of the different X-rays 4.

Now, experiment examples and embodiments of the invention using the X-ray diffraction systems having the above constructions will be described in detail.

(EXPERIMENT EXAMPLE 1)

(1-1) First, using p-type silicon single crystals grown by the Czochralski process and having resistivities and interstitial oxygen concentrations Oi(b) as shown in Table 1, a total of 36 sample wafers having four different thickness were prepared.

(1-2) Before heat treatment, the resistivity and the interstitial oxygen concentration Oi(b) of each sample was measured by using four points probe method and FT-IR, respectively.

(1-3) Further, before the heat treatment, the intensity of the diffracted X-rays of each sample was measured by both the Laue and Bragg cases. For the measurements, a current of 1 A with an accelerating voltage of 55 KV was applied to X-ray source 7. The angle of each sample with respect to the incident X-ray beam, was adjusted such that the 440 and 400 diffraction Bragg conditions in the Laue and Bragg cases, respectively, were satisfied by the characteristic X-rays Kα1 (with wavelength of 0.0709 nm) of a molybdenum (Mo) target. Then, the diffracted X-ray intensity was measured with the scintillation counter 5.

(1-4) The diffracted X-ray intensities Xb (in $10^3$ cps) obtained in the above measurements in (1-3) are shown in Table 1.

(1-5) As shown in Table 1, in the Laue case, the diffracted X-ray intensity is concentrated in 7,000, 6,800, 6,000 and 5,500 cps with sample thickness of 440, 510, 630 and 690 μm, respectively. In the Bragg case, it is concentrated at 12,000 cps in a thickness range of 440 to 690 μm.

It will be seen that the diffracted X-ray intensity of wafer which has not been heat treated, is not substantially influenced by the initial interstitial oxygen concentration and resistivity; in the Laue case it is approximately dependent on the sole sample thickness, and in the Bragg case it is not dependent on the sample thickness T but is fixed.

Thus, once the diffracted X-ray intensity (for each sample thickness T in the Laue case) is measured, the measured value of Xb can be used as a fixed value.

TABLE 1

| Wafer thickness (μm) | Resistivity (Ω cm) | Oi(b) (ppma-JEIDA) | Diffracted X-ray intensity Xb ($10^3$ cps) | |
|---|---|---|---|---|
| | | | Laue case (440) | Bragg case (400) |
| 440 | 0.3 to 0.5 | 13 to 14 | 7.2 | 11.6 |
| | | 18 to 19 | 7.1 | 11.9 |
| | | 23 to 24 | 6.9 | 12.2 |
| | 5 to 7 | 13 to 14 | 6.9 | 12.3 |
| | | 18 to 19 | 6.8 | 11.8 |
| | | 23 to 24 | 7.2 | 12.0 |
| | 20 to 22 | 13 to 14 | 6.8 | 11.6 |
| | | 18 to 19 | 6.9 | 11.9 |
| | | 23 to 24 | 7.0 | 11.8 |
| 510 | 0.3 to 0.5 | 13 to 14 | 6.6 | 12.2 |
| | | 18 to 19 | 6.8 | 12.1 |
| | | 23 to 24 | 7.0 | 11.8 |
| | 5 to 7 | 13 to 14 | 6.7 | 11.6 |
| | | 18 to 19 | 7.1 | 12.4 |
| | | 23 to 24 | 6.8 | 11.9 |
| | 20 to 22 | 13 to 14 | 6.7 | 12.1 |
| | | 18 to 19 | 6.8 | 12.0 |
| | | 23 to 24 | 6.8 | 12.3 |
| 630 | 0.3 to 0.5 | 13 to 14 | 5.8 | 11.8 |
| | | 18 to 19 | 5.9 | 11.9 |
| | | 23 to 24 | 6.2 | 11.7 |
| | 5 to 7 | 13 to 14 | 6.0 | 11.9 |
| | | 18 to 19 | 5.9 | 12.3 |
| | | 23 to 24 | 6.1 | 11.8 |
| | 20 to 22 | 13 to 14 | 5.8 | 12.4 |
| | | 18 to 19 | 6.3 | 11.7 |
| | | 23 to 24 | 5.9 | 11.8 |
| 690 | 0.3 to 0.5 | 13 to 14 | 5.6 | 12.1 |
| | | 18 to 19 | 5.3 | 12.2 |
| | | 23 to 24 | 5.4 | 12.3 |
| | 5 to 7 | 13 to 14 | 5.4 | 11.9 |
| | | 18 to 19 | 5.4 | 11.6 |
| | | 23 to 24 | 5.7 | 12.4 |
| | 20 to 22 | 13 to 14 | 5.6 | 11.6 |
| | | 18 to 19 | 5.6 | 11.9 |
| | | 23 to 24 | 5.5 | 12.3 |

(EXPERIMENT EXAMPLE 2)

(2-1) The 36 different sample wafers that were used in Experiment example 1 were heat treated in a nitrogen ambient at 800° C. for 4 hours and also in a dry oxygen ambient at 1,000° C. for 16 hours.

(2-2) With the 36 sample wafers after the heat treatment, the diffracted X-ray intensities Xa in the Laue and Bragg cases were measured by the method as in (1-3) in Experiment example 1.

(2-3) The interstitial oxygen concentration Oi(a) of each of the 36 samples after the heat treatment was measured by the FT-IR process, and for each sample wafer the amount of precipitated oxygen ΔOi was calculated from the difference between Oi(a) and the interstitial oxygen concentration Oi(b) before the heat treatment, which had been obtained by the measurement in (1-2) in Experiment example 1.

(2-4) Further, for each of the above 36 different sample wafers the diffracted X-ray intensity ratio was calculated, which is the division of the different X-ray intensity Xa after the heat treatment as determined in the measurement in (2-2) above by the diffracted X-ray intensity Xb before the heat treatment having been determined in (1-3) in Experiment example 1.

(2-5) A plot was drawn as in the graph of FIG. 3 by taking the ordinate for the diffracted X-ray intensity ratio Xa/Xb in the Laue case and taking the abscissa for the precipitated oxygen amount $\Delta Oi$ obtained in (2-3) above.

It will be seen from the graph that in the Laue case the diffracted X-ray intensity ratio Xa/Xb is in a good correlation with the amount of precipitated oxygen $\Delta Oi$, and it is confirmed that using a coefficient A the ratio is approximately expressed by the following equation (1).

$$Xa/Xb = A\Delta Oi + 1 \quad (1)$$

If the wafer thickness is constant, Xb is also constant. In this case, the equation (1) can be re-written as the following equation (2).

$$Xa - Xb = AXb \cdot \Delta Oi \quad (2)$$

(2-6) A plot was drawn as in the graph of FIG. 3 by taking the ordinate for the diffracted X-ray intensity ratio Xa/Xb in the Bragg case and the abscissa for the amount of precipitated oxygen $\Delta Oi$ obtained in (2-3) above.

It will be seen from the graph that in the Bragg case the diffracted X-ray intensity ratio Xa/Xb is in a good correlation with the amount of precipitated oxygen $\Delta Oi$, and it is confirmed that using a coefficient B the ratio is approximately expressed as the following equation (3).

$$Xa - Xb = B\Delta Oi + 1 \quad (3)$$

Further, since Xb is constant as shown by the result in Experiment example 1, in the Bragg case the equation (3) can be re-written as the following equation (4).

$$Xa - Xb = BXb \cdot \Delta Oi \quad (4)$$

(Embodiment 1)

(3-1) A boron-doped p-type silicon single crystal with a resistivity of 10 to 12 $\Omega$cm was obtained by the Czochralski process, and five wafers with a thickness of 510 µm were produced from the same region of the single crystal.

(3-2) Of these five wafers, the interstitial oxygen concentration Oi(b) before heat treatment was measured by the FT-IR process.

(3-3) Subsequently, the five wafers were heat treated in the manner as in (2-1) in Experiment example 2.

(3-4) Then, of the five wafers having been heat treated the diffracted X-ray intensities in the Laue and Bragg cases were measured in the manner as in (1-3) in Experiment example 1.

(3-5) Also, of the five heat treated wafers the interstitial oxygen concentration Oi(a) was measured by the FT-IR process. Then, from the difference of the measured value and the interstitial oxygen concentration before and after the heat treatment, the amount of precipitated oxygen $\Delta Oi$ was calculated. The average value obtained with the five wafers was 8.4 ppma-JEIDA.

(3-6) Of the wafer with a thickness of 510 µm having been obtained in Experiment example 1, the diffracted X-ray intensity ratio Xa/Xb in the Laue case, was calculated from the diffracted X-ray intensity Xb (of 6,800 cps) before the heat treatment and that Xa after the heat treatment as measured in (3-4) above. The average value obtained with the five wafers was 7.7.

The amount of precipitated oxygen $\Delta Oi$ was determined from this diffracted X-ray intensity ratio of 7.7 and the correlation in the Laue case as shown in FIG. 3, and it was 8.6 ppma-JEIDA, which was in good accordance with the value obtained in the FT-IR process in (3-5) above.

(3-7) In the Bragg case, the diffracted X-ray intensity ratio Xa/Xb was calculated from the diffracted X-ray intensity Xb (12,000 cps) before the heat treatment as already obtained in Experiment example 1 and the diffracted X-ray intensity Xa after the heat treatment determined in the measurement in (3-4) above. The average value obtained with the five wafers was 3.1.

The amount of precipitated oxygen $\Delta Oi$ was obtained from this diffracted X-ray intensity ratio of 3.1 and the Bragg case correlation shown in FIG. 3, and it was 8.3 ppma-JEIDA which was in good accordance with the value obtained in the FT-IR process in (3-5) above.

(Embodiment 2)

(4-1) A boron-doped p-type silicon single crystal with a resistivity of 0.04 to 0.05 $\Omega$cm was obtained with the Czochralski process, and five wafers with a thickness of 510 µm and two wafers with a thickness of 100 µm were produced from the same region of the single crystal.

(4-2) In the case of silicon single crystal having a resistivity of 0.04 to 0.05 $\Omega$cm, accurate FT-IR measurement on thick wafers can not be done because of the absorption of infrared light by excess free carries in the crystal. Accordingly, the wafers with thickness of 100 µm were used for the measurement of the interstitial oxygen concentration Oi(b) before the heat treatment using the FT-IR process, and this value (i.e., average value of the two wafers) was used as the interstitial oxygen concentration Oi(b) of the other five wafers with thickness of 510 µm.

(4-3) Subsequently, the five wafers were heat treated in the manner as in (2-1) in Experiment example 2.

(4-4) Of these five wafers, the diffracted X-ray intensities Xa after the heat treatment in the Laue and Bragg cases were then measured with the manner as in (1-3) in Experiment example 1.

(4-5) After the measurement in (4-4) above, the five wafers were chemically etched to reduce their thickness from 510 to 100 µm. Then, their interstitial oxygen concentration Oi(a) after the heat treatment was measured by the FT-IR Process. Thereafter, the amount of precipitated oxygen $\Delta Oi$ was calculated from the difference of the measured value and the interstitial oxygen concentration Oi(b) before and after the heat treatment. The average value with the five wafers was 12.7 ppma-JEIDA.

(4-6) Then, the diffracted X-ray intensity ratio Xa/Xb in the Laue case was calculated with the wafers having thickness of 510 µm obtained in Experiment example 1 from the diffracted X-ray intensity Xb (6,800 cps) before the heat treatment and the diffracted X-ray intensity Xa after the heat treatment as determined in the measurement in (4-4) above. The average value obtained with the five wafers was 11.0.

The amount of precipitated oxygen $\Delta Oi$ was obtained from this diffracted X-ray intensity ratio of 11.0 and the Laue case correlation shown in FIG. 3, and it was found to be 12.8 ppma-JEIDA, which was in good accordance with the value obtained in (4-5) above.

(4-7) The diffracted X-ray intensity ratio Xa/Xb in the Bragg case was obtained from the diffracted X-ray intensity Xb (12,000 cps) before the heat treatment as determined in Experiment example 1 and that X-ray after the heat treatment determined in the measurement in (4-4) above. The average value obtained with the five wafers was 4.3.

The amount of precipitated oxygen $\Delta Oi$ was obtained from this diffracxted X-ray ratio of 4.3 and the Bragg case correlation shown in FIG. 3, and it was found to be 12.8 ppma-JEIDA was in good accordance with the value obtained in (4-5) above.

As has been shown, in the method of evaluating silicon single crystal according to the invention, the diffracted X-ray intensity of a silicon wafer which has not been heat treated, is hardly influenced by the initial interstitial oxygen concentration nor resistivity. Instead, in the Laue case it approximately depends on the sole thickness T, and in the Bragg case it is fixed irrespective of the sample thickness T. It will thus be seen that the diffracted X-ray intensity once measured can be utilized as a fixed value.

Thus, it is possible to preserve the data about the diffracted X-ray intensity Xb before the heat treatment by collecting the data in advance in both the Laue and Bragg cases.

Further, the diffracted X-ray intensity ratio Xa/Xb obtained by dividing the diffracted X-ray intensity Xa after heat treatment by the intensity Xb before the heat treatment or the diffracted X-ray intensity difference (Xa–Xb) obtained by subtracting Xb from Xa and the amount of precipitated oxygen ΔOi are in a good correlation, and thus it is possible to prepare the correlation in advance. Thus, for obtaining the amount of precipitated oxygen ΔOi of a sample silicon wafer, the ratio Xa/Xb or the difference (Xa–Xb) between diffracted X-ray intensities is calculated using preliminary obtained Xb and newly measured Xa, after the measurement of the diffracted X-ray intensity Xa of the heat treated sample wafer. Then the amount of precipitated oxygen ΔOi can be determined from the preliminary obtained correlation between the ratio Xa/Xb or the difference (Xa–Xb) and the amount of precipitated oxygen ΔOi.

In the Laue case, diffracted X-rays can be determined in the direction of the entire thickness of sample, and it is thus possible to determine the precipitated oxygen amount ΔOi in the direction of the entire thickness.

In the Bragg case, the penetration depth of X-rays from the incidence surface thereof is X-ray extinction distance (i.e., the distance by which the X-ray intensity is reduced to 1/e). Thus, it is possible to determine the amount of precipitated oxygen ΔOi in a superficial region up to this depth.

The above embodiments have concerned with the 440 and 400 diffractions. However, the inventor has confirmed that the same effects are obtainable as well with 220, 660, 880, 400, 800 and 1200 in the Laue case and 800 and 1200 in the Bragg case.

That is, the diffraction used is by no means limited to the 440 and 400 diffractions, but it can be altered variously within the limits of without departing from the subject matter of the invention. For example, in the Laue case, as the indexes of the particular lattice plane designated as hkl, h, k and l may be designated by an even number excluding zero, an even number including zero and zero, respectively. In the Bragg case, h may be an even number excluding zero, and k and l may be diffractions at the lattice plane which are designated by zero.

As has been shown in detail, in contrast to the prior art example, in which the interstitial oxygen concentration of a silicon wafer is measured before and after heat treatment for using the concentration difference for precipitated oxygen amount determination, even with a silicon wafer which has been heat treated, it is possible to calculate the amount of precipitated oxygen by merely measuring the diffracted X-ray intensity.

It is to be particularly noted that it has been confirmed by the inventor that there is a good correlation between the amount of precipitated oxygen and the diffracted X-ray intensity ratio or difference and that the diffracted X-ray intensity of the silicon wafer not heat treated is hardly influenced by the initial oxygen concentration nor resistivity, and substantially the same with silicon single crystals which are the same or substantially the same in the thickness, that is, the diffracted X-ray intensity of the silicon wafer not heat treated has a fixed value appropriately dependent on the thickness of wafer.

Thus, it is possible to prepare in advance data of diffracted X-rays corresponding to known thickness of silicon wafer which has not been heat treated. Further, it is possible to prepare the correlation between the intensity ratio or difference between the prepared diffracted X-ray intensity and the diffracted X-ray intensity after heat treatment and the corresponding amount of precipitated oxygen.

After the heat treatment, the intensity of diffracted X-rays produced by Bragg diffraction at a particular lattice plane of silicon wafer is measured. Then, the diffracted X-ray intensity ratio or difference is calculated from the measured value and the diffracted X-ray intensity before the heat treatment of the silicon wafer. Then, the amount of precipitated oxygen is calculated from the correlation between the already obtained diffracted X-ray intensity ratio or difference and the amount of precipitated oxygen.

Further, by irradiating the front surface of a silicon wafer with X-rays, taking out diffracted X-rays produced by Bragg diffraction at a particular lattice plane from a surface different from the incidence surface for diffracted X-ray intensity measurement and then calculating the amount of precipitated oxygen, it is possible to measure the amount of precipitated oxygen originated from the diffracted X-ray intensity in the direction of entire thickness of sample.

Further, by irradiating the front surface of a silicon wafer with X-rays, taking out diffracted X-rays produced Bragg diffraction at a particular lattice plane from the same surface as the incidence surface for diffracted X-ray intensity measurement and then calculating the amount of precipitated oxygen, it is possible to measure the amount of precipitated oxygen due to the diffracted X-ray intensity from a superficial region of sample up to a certain depth from the incidence surface without making the sample thinner.

What is claimed is:

1. A method of evaluating a silicon single crystal comprising the steps of;

irradiating frontside surface of a preliminary heat treated sample silicon wafer with X-rays, taking out diffracted X-rays produced by Bragg diffraction at a particular lattice plane in said silicon wafer from backside surface, measuring the intensity of said diffracted X-ray, thereby preparing a correlation between the diffracted X-ray intensity and amount of precipitated oxygen of silicon wafers, characterized in:

measuring the diffracted X-ray intensity of the heat treated sample silicon wafer and calculating the amount of precipitated oxygen thereof from the prepared correlation.

2. The method of evaluating a silicon single crystal according to claim 1, wherein the particular lattice plane is designated by hkl, where an even number excluding zero, an even number including zero and zero, respectively.

3. The method of evaluating a silicon single crystal according to claim 2, wherein the index of the particular lattice plane is 220, 440, 660, 880, 400, 800 or 1200.

4. The method of evaluating a silicon single crystal according to claim 1, wherein the prepared correlation is a relation between the ratio or difference of the diffracted X-ray intensity before and after the heat treatment and the amount of precipitated oxygen under an assumption that the thickness of the silicon wafer is approximately same before and after the heat treatment.

5. A method of evaluating a silicon single crystal comprising the steps of;

irradiating frontside surface of a preliminarily heat treated sample silicon wafer with X-rays, taking out diffracted X-rays produced by Bragg diffraction at a particular lattice plane in said silicon wafer from the same surface as the incidence surface, measuring the intensity of said diffracted X-ray, thereby preparing a correlation between the diffracted X-ray intensity and amount of precipitated oxygen of silicon wafers, characterized in:

measuring the diffracted X-ray intensity of the heat treated sample silicon wafer and calculating the amount of precipitated oxygen of thereof from the prepared correlation.

6. The method of evaluating a silicon single crystal according to claim 5, wherein the particular lattice plane is designated by hkl, where h, k and l are indexes designated by an even number excluding zero, an even number including zero and zero, respectively.

7. The method of evaluating a silicon single crystal according to claim 6, wherein the index of the particular lattice plane is 400, 800 or 1200.

8. The method of evaluating a silicon single crystal according to claim 5, wherein the prepared correlation is a relation between the ratio or difference of the diffracted X-ray intensity before and after the heat treatment and the amount of precipitated oxygen.

* * * * *